United States Patent
Marin et al.

(10) Patent No.: US 10,582,961 B2
(45) Date of Patent: Mar. 10, 2020

(54) METHOD AND DEVICE FOR COSMETICALLY TREATING DARK SPOTS ON THE SKIN BY MEANS OF CRYO-CYTO-SELECTIVE CRYOGENICS

(71) Applicant: Cryobeauty, Chartres (FR)

(72) Inventors: Denis Marin, L'Etang la Ville (FR); Dominique Pacito, Cachan (FR)

(73) Assignee: Cryobeauty, Chartres (FR)

( * ) Notice: Subject to any disclaimer, the term of this patent is extended or adjusted under 35 U.S.C. 154(b) by 186 days.

(21) Appl. No.: 15/326,300

(22) PCT Filed: Jan. 13, 2016

(86) PCT No.: PCT/EP2016/050565
§ 371 (c)(1),
(2) Date: Jan. 13, 2017

(87) PCT Pub. No.: WO2016/113305
PCT Pub. Date: Jul. 21, 2016

(65) Prior Publication Data
US 2017/0354451 A1    Dec. 14, 2017

(30) Foreign Application Priority Data
Jan. 13, 2015  (EP) .................... 15305022

(51) Int. Cl.
*A61B 18/02*  (2006.01)
*A61B 18/00*  (2006.01)
*A61B 17/00*  (2006.01)

(52) U.S. Cl.
CPC ............ *A61B 18/0218* (2013.01); *A61B 2017/00747* (2013.01); *A61B 2018/0047* (2013.01);
(Continued)

(58) Field of Classification Search
CPC ...... A61B 18/0218; A61B 2017/00747; A61B 2018/00452; A61B 2018/0047; A61B 2018/00714; A61B 2018/00744
(Continued)

(56) References Cited

U.S. PATENT DOCUMENTS 5,738,682 A * 4/1998 Jensma .............. A61B 18/0218
606/20
5,997,530 A  12/1999 Nelson et al.
(Continued)

FOREIGN PATENT DOCUMENTS

FR  2885059 A  11/2006
FR  2885539 A  11/2006

OTHER PUBLICATIONS

International Search Report and Written Opinion issued by European Patent Office, acting as the ISA, for International Application PCT/EP2016/050565 dated Mar. 4, 2016.

*Primary Examiner* — Michael F Peffley
(74) *Attorney, Agent, or Firm* — McCarter & English, LLP

(57) ABSTRACT

The invention relates to a method for cosmetically treating dark spots on the skin, wherein said method is intended for eliminating at least one of said dark spots located in a region of the hand, the face, the limbs or the chest area of a person suffering from such skin hyperpigmentation, characterised in that said method includes a step of applying a spray of cryogenic fluid to said region, which brings the skin temperature to a temperature of between −4° C. and −15° C. for a consecutive application period of from 2 to 10 seconds, in order to selectively act on the melanocytes, and to a device for carrying out said method.

7 Claims, 4 Drawing Sheets

(52) U.S. Cl.
CPC .............. *A61B 2018/00452* (2013.01); *A61B 2018/00714* (2013.01); *A61B 2018/00744* (2013.01)

(58) Field of Classification Search
USPC ...................................... 606/20–26
See application file for complete search history.

(56) References Cited

U.S. PATENT DOCUMENTS

| | | | |
|---|---|---|---|
| 6,141,985 A * | 11/2000 | Cluzeau | A61B 18/0218 606/22 |
| 6,226,996 B1 | 5/2001 | Weber et al. | |
| 6,960,202 B2 * | 11/2005 | Cluzeau | A61B 18/0218 606/20 |
| 7,963,959 B2 * | 6/2011 | Da Silva | A61B 18/0218 606/20 |
| 8,562,597 B2 * | 10/2013 | Van Der Heijden | A61B 18/0218 222/402.1 |
| 2004/0102768 A1 | 5/2004 | Cluzeau et al. | |
| 2007/0005048 A1 | 1/2007 | Niedbala et al. | |
| 2010/0087806 A1 * | 4/2010 | Da Silva | A61B 18/0218 606/22 |

* cited by examiner

METHOD AND DEVICE FOR COSMETICALLY TREATING DARK SPOTS ON THE SKIN BY MEANS OF CRYO-CYTO-SELECTIVE CRYOGENICS

CROSS-REFERENCE TO RELATED APPLICATIONS

This application is the National Stage entry under 35 U.S.C. § 371 of International Application Number PCT/EP2016/050565 filed on Jan. 13, 2016, published on Jul. 21, 2016 under publication number WO 2016/113305 A1, which claims the benefit of priority under 35 U.S.C. § 119 of European patent application number 15305022.4 filed Jan. 13, 2015.

TECHNICAL FIELD OF THE INVENTION

The invention relates to a method for the cosmetic treatment of dark spots on the skin and is intended to eliminate said dark spots on the hands, face, limbs or chest of a person suffering from such skin hyperpigmentation on the one hand and, a device for the application of said method on the other hand.

Melanogenesis, by means of specialised cells called melanocytes, at the origin of skin colour, is influenced by external factors that increase the production of melanin and, as a result, a localised darker colour. This gives rise to the formation of dark spots on the skin.

Dark spots (lentigines, actinic dermatitis) may appear as of the age of 30 years, sometimes as of adolescence, and are mainly located on the hands, face and chest. In particular, they result from over-exposure to the sun. Skin ageing refers to all of the consequences of the sun on the skin, such as blemishes, sagging skin, wrinkling, a wrinkled appearance and dry skin. This may occur on the spots by:

sun spots or "freckles", whose number and intensity increase with exposure to ultraviolet light;
solar lentigos of the areas overexposed to the sun;
hyperchromia (abnormal pigmentation) such as melisma, whose intensity is directly related to exposure to ultraviolet A and B;
"perfume dermatitis" resulting from photosensitisation induced by a perfume.

Intrinsic skin ageing causes atrophy accompanied by sagging skin, dryness and pigmentation disorders. The main pigment disorder is senile lentigo appearing towards the age of fifty on the exposed parts of the skin and, more specifically, on the back of the hands and sometimes on the face. Small, smooth, flat, dark spots, ranging from several millimetres to severs centimetres in diameter. The prognosis is always benign. These spots may also develop in the elderly person, due to inflammation or hormonal imbalance.

They are considered to be more or less aesthetic depending on the intensity of the hyperpigmentation. The original cause is poorly known. The physiological consequences have been better studied: (1) increase in the synthesis of melanin, (2) acceleration of the transfer of melanin from the melanosomes to the keratinocytes and finally (3) the faster migration of the melanocytes to the skin surface.

STATE OF THE PRIOR ART

Two means of treatment are possible: the reduction in the hyperpigmentation or the destruction of the melanin or the hyper-pigmented tissue.

The hyperpigmentation may be reduced by de-pigmenting agents with a pharmacological action, that act on the physiological consequences. By way of example, we can mention; hydroquinone monomethyl ether, mequinol, tretinoin or kojic acid. The length of treatment is long and the means of application are constraining (several applications per day). Therefore, the compliance is low. In addition, the risk of recurrence is very high since the original cause has not be dealt with. The patient can carry out this treatment at home and the help of a dermatologist is not necessary. The secondary and adverse effects are mainly local inflammatory reactions, allergic reactions to the active ingredients and a burning sensation with certain active ingredients.

Topical steroids have a certain depigmenting potential, especially when applied under an occlusive dressing. They are used in hydroquinone creams although this is more to reduce the irritation resulting from the preparation than to increase the efficacy. Hydroquinone monobenzyl ether should be avoided at all costs. Indeed, it is very powerful and unwieldy and often produces depigmentation at a distance from the treated area. In the past, it has resulted in severe cosmetic accidents, with definitive leukomelanoderma. Some practitioners still use it in the treatment of extensive vitiligos to complete the depigmentation of the areas of healthy skin. However, this requires two applications per day over several months with a concentration of 5 to 20%. In addition, this product may be irritating or allergic.

The destruction of the melanin or more generally the hyper-pigmented tissue is based on cryotherapy carried out by the dermatologist, that is, the application of cold on the surface to treat by a health professional. This classic and ancient professional technique does not allow for the control of the level or length of exposure at the temperature obtained.

Indeed, the dermatologist uses a cylinder to spray gases that in general are at very low temperatures such as liquid nitrogen at −196° C., without being able to precisely control the flow and the spraying time since they mechanically trigger the opening of the cylinder of cryogenic gas. By convention, doctors have defined durations for the application of the cold based on the type of problem to treat, but without any other precision.

Therefore, the liquid nitrogen should be applied on a common wart once for 10 seconds, on a plantar wart twice between 20 and 30 seconds and on a solar lentigo once for 5 seconds. The lack of precision and control of the duration of the application of the cold and the level of the very low temperatures to apply results in a major disparity in treatments, a total lack of reproducibility and therefore, considerable variations in the efficacy obtained.

In addition, the use of liquid nitrogen (−196° C.) provokes a second-degree burn, resulting in necrosis of the entire population of the cells in the treated tissue, without any differentiation, resulting in residual scarring, increased risk of hypo-pigmentation and pain upon application.

The other techniques consist of peeling and microdermabrasion that superficially attenuate the colour of the dark spot without eliminating it, and finally, laser treatment that has the same disadvantages as that of cryotherapy.

Conventional cryotherapy is used on certain skin lesions, such as actinic lentigos. The technique is highly variable depending on the equipment used to apply the cold. Dermatologists mainly spray liquid nitrogen on the surface to destroy. The sprays may be open or closed, the nitrogen projected in neophrene cones whose size is adapted to the area to treat. This method often follows curettage of the area to treat so as to be able to take a sample for a histological examination and more precisely determine the boundaries of the extension so as to optimise the results. One or several freeze-thaw cycles are thereby carried out and, in general, two cycles are carried out.

Another method consists of applying liquid nitrogen by means of closed cryodes whose size is adapted to the target surface. Control of the intra-tissue temperature using needles, thermocouple or impedanziometry is possible but not systematically used. The existence of a freezing halo at the periphery of the target area and the freezing and thawing times are used to assess tissue destruction. This is a relatively simple, ambulatory technique that can be used to treat multiple lesions and is not counter-indicated for patients on anticoagulants. The cryonecrosis evolves over several weeks and requires the change of dressings. It may give rise to hypo- or hyper-pigmented dyschromaic sequelae.

When the dark spots are abundant or very big, a treatment with liquid nitrogen is too violent and it is preferable to use, for example, dry ice or N20.

U.S. Pat. No. 7,963,959 describes an automated device guided by a system of image acquisition for the treatment of many skin areas using a variety of fluids for cryotherapy, including CFCs. This device is intended for use in a medical setting.

Patent applications FR 2 885 059 and FR 2 885 539 describe manual devices used to apply a cryogenic fluid in a supply of aerosol on an area of the skin to be treated, via a nozzle and an ejection nozzle. A mechanical timer controls the length of exposure. These devices are designed to enable treatment outside of a hospital or medical environment. However, management of the flow of fluid and length of application have been found to be, in practice, not controlled, little reliable and difficult to reproduce. Indeed, the structure of the device itself (a large number of components), the interactions and the mechanical and thermic tolerance of the different components and the way it has been designed make the application of cryogenic fluid difficult to reproduce. Indeed, these applications give rise to significant variations in the local instantaneous temperature of the areas treated from one trial to the next due to this lack of reproducibility and do not provide the safety and efficacy expected of this type of device because of the major risk of burns and extensive necrosis.

Moreover, the implementation of prior art devices produces a non-selective cell lysis effect, that is, they produce necrosis of the entire cell population of the tissue of the treated areas, and this is undifferentiated on all cell populations (melanocytes, keratinocytes, fibroblasts, etc.). Indeed, their intrinsic nature or operating mechanisms and implementation do not enable the precise management or control of the dose delivered and the length of application of the cryogenic fluid on a given area or, as a consequent, the level of the desired temperature over the entire treated area. Since the range of temperatures actually applied on the tissue is extensive, this method does not provide a cryo-cyto-selective action on the cell populations present. However, a cryo-selective action is the ability to act specifically on a given population of cells (for example, only melanocytes), without acting on other cell populations. Therefore, the devices in the prior art do not act only on one cell population (for example melanocytes). This requires a very precise control of the temperature applied on the cells and not only at the lowest possible temperature obtained but also on the kinetics of the temperature variation. Indeed, since certain cell populations react differently to cold than others, by applying cold within a certain temperature range and according to a certain kinetics, it is then possible to act specifically on a given population of cells by provoking their lysis, without affecting other populations. The application of cold to obtain a cyto-selective effect is called cryo-cyto-selective action or cryo-cyto-selectivity.

Until now, the skilled person only looked for undifferentiated local cell necrosis since they only took into account the length of time, as they were not familiar with cryo-cyto-selectivity. As a result, the skilled person did not think and could not imagine means to obtain a cyto-selective cryogenic action for a cosmetic treatment. In addition, devices were not available for out-patient use, were not simple or fast to implement and allow for very precise automated control of the optimum temperature that was sufficient to reach the target area.

Moreover, the known traditional cryogenic devices experience problems of icing and clogging due to the sudden freezing of the water vapour present in the immediate vicinity of the nozzle when the cryogenic fluid is triggered. These problems are exacerbated by the nature of the non-hydrophobic materials used until now for the nozzle.

This phenomenon is especially of concern because the nozzle whose diameter must be very small over a considerable length is generally made of metal, for reasons of mechanical strength.

As a result, the nozzle of current cryogenic devices enabling the timing of the flow of fluid is the seat of physical phenomena of retention and conduction of the upstream cold that disrupt the operation of the means of delay, whether mechanical (springs, cams, etc.) or electronic (solenoid valve, etc.) because they are all very sensitive to low temperatures.

In addition, the skilled person is faced with technical issues of regulating the power and extent of the coolant fluid. Indeed, when they use a pressurised container, they have to trigger a lever to open or close a valve that determines the output of the coolant. The time of application is extremely variable from one spray to the next and, as a result, the dose of cold delivered cannot be controlled. Finally, a screw on the nozzle to alter the flow does not, after a change, allow the position of the earlier flow to be found.

These problems have a very significant impact on the distribution of the cryogenic fluid and, as a result, on the temperature kinetics obtained on the treated tissue. It is not possible today, with existing devices, to produce only cosmetic effects by selective cyto-cryogenics.

PRESENTATION OF THE INVENTION

In view of the techniques and products currently used, the invention aims at solving the technical problems raised by the prior art by providing:
the total elimination of dark spots and not by reducing their colour,
obtaining an immediate effect,
eliminating dark spots with one application
obtaining the expected results without creating marks on the skin, without causing pain and redness during and after the application of the cold,
eliminating all risks of frost and/or conduction of cold by the nozzle to avoid any disturbance of the system of electronic or mechanical timing of the cryogenic device,
limiting and controlling the flow of coolant,
perfectly mastering the temperature level to achieve and maintain at the surface of the skin over a given time (temperature kinetics),
allowing easy and fast use of the device.

For this purpose, the invention provides a cosmetic treatment method according to claim 1.

The treatment according to the invention generates a cyto-selective action through appropriate cryogenics. In the context of the invention, the term selective cyto-cryogenic action or cryo-cyto-selectivity refers to the fact of acting selectively by means of a cooling agent on a population of cells of a tissue considered, without affecting other cell populations. The cosmetic treatment method according to the invention acts only by a controlled level of cold, on melanocytes located between the stratum corneum and the basal level (dermal-epidermal junction), in the epidermis. With the stratum corneum, the epidermis is the most superficial part of the skin. Thus, this superficial action occurs without destroying the keratinocytes.

The invention provides a cyto-selective cryogenic device for the implementation of this method according to claim 10.

Ways to carry out this method and the device in the invention are defined by the other claims.

BRIEF DESCRIPTION OF THE FIGURES

Other characteristics and advantages of the invention will emerge on reading the description that follows, with reference to the accompanying figures, which illustrate.

DETAILED DESCRIPTION OF THE EMBODIMENTS

Figure 1:
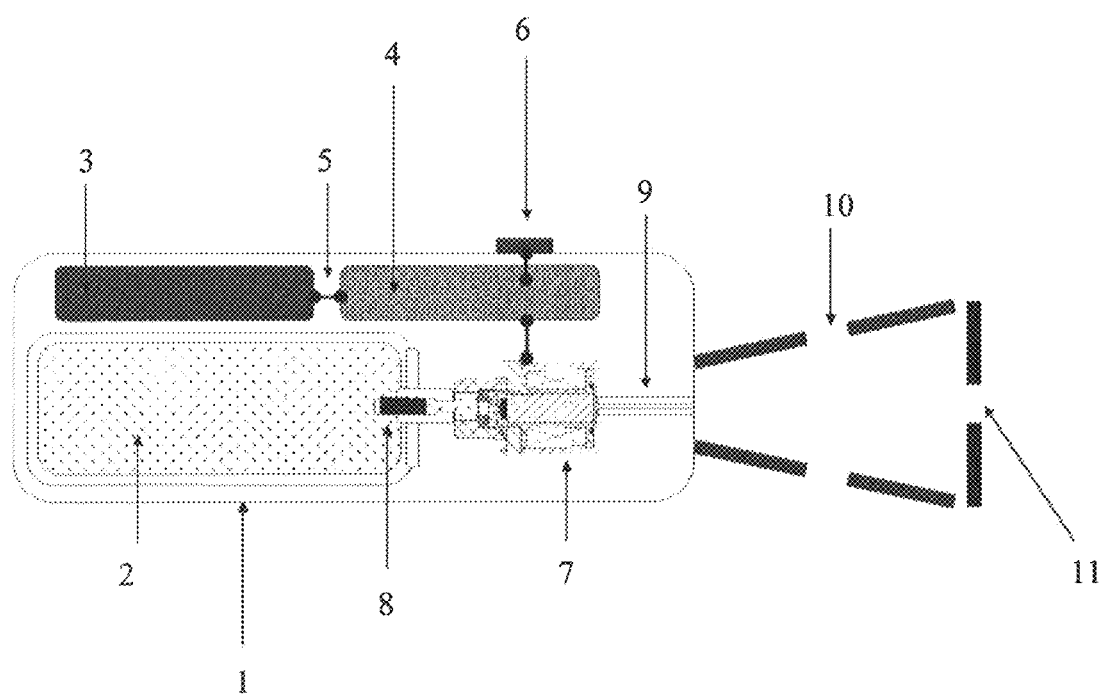
FIG. 1 is a schematic view in longitudinal section of an embodiment of the cyto-selective cryogenic device according to the invention.

Cryotherapy is a method that is considered to be painful in 64% of the patients treated when the cold is applied for over 10 seconds. If the cold is applied for under 10 seconds, 44% of the patients do not perceive any pain. The lower the time of application, the lower the pain. However, a low exposure to cold considerably reduces the efficacy of the treatment since, in such a case, only 30% of the patients are cured. It is clear that the time of cold application has a direct impact on the efficacy of the treatment and the intensity of the pain experienced.

The cooling of tissue leads to changes in the physical state and, according to the conditions for the application of the cold, its preservation or, on the contrary, its alteration. The thermal shock applied in the context of the invention is a highly considerable reduction in the temperature in a minimum of time. The procedure is implemented by very rapid freezing, followed by slow warming in which the action of the cold persists. The very sudden reduction in the temperature induces, even before the tissue is solidified, the microcrystallisation of the intracellular water. These microcrystals induce membrane alterations, denaturation of structural proteins and enzymes, excessive concentration of ions, all conditions resulting in an adverse effect on the cells. Recrystallisation of the excess water during the heating phase further increases cell lysis. In normal conditions, the skin temperature is about 34° C. This is the temperature that must be lowed to the maximum in a minimum time.

The melanocytes are located at the dermo-epidermal junction and migrate during the fours stages of their maturation to the surface of the skin, that is, to the superficial layer of the epidermis. These melanocytes contain melanosomes, vesicles containing melanin. The maturation of the melanosomes and the melanin concentration occurs within the melanocytes. The melanosomes are then transferred to the dendrites of the melanocytes and to the keratinocytes, which integrate them in their cell structures. They place themselves above the nucleus to protect it from UV radiation. Enzymes then break down the melanosomes. The released melanin is eliminated at the epidermal surface by desquamation of the stratum corneum and in the dermis by the lymphatic route.

Hyperpigmentation results from a melanogenesis disorder, with increased activity in the melanosomes and sometimes the more extensive transfer of pigment in the keratinocytes of the stratum spinosum, or an accumulation of melanin in the dermis. It thereby consists of a hypermelanocytose, located at the basal level. The hypermelanocytose is characterised by the increase in the number of melanocytes, or an increase in the melanin synthesis by the melanocytes. The key cell and, consequently, the target cell is the melanocyte. However, the keratinocytes should not be affected since they protect the epidermal tissue from UV radiation.

The thickness of the epidermis varies according to the area concerned, from 0.02 mm on the facial skin to 0.5 mm on the soles of the feet. Its average thickness is 0.01 mm. On the hands (top of the hands), the melanocytes are located 0.1 mm from the surface of the skin.

In an epidermis subjected to cold, the melanocytes remain viable if they are subjected to a temperature between 0 and −4° C.

Between −4° C. and −7° C., granuloma lysis containing pigments is observed, that is, the melanosomes containing melanin, followed by the beginning enzyme digestion of the melanin in the melanocytes and in the keratinocytes in the deep layer of the epidermis, near the basal layer.

Between −7° C. and −30° C., the disappearance of the melanocytes is observed and, below, the melanocytes do not reappear (depigmentation disorder). The destruction of keratinocytes occurs at temperature below −20° C., with a very significant destruction of highly differentiated melanocyte populations.

The invention has shown that the efficacy of the cosmetic treatment of hyperpigmentation due to melanocytes, without significant damage to the keratinocytes, occurs at a range of −4° C. and −15° C. and preferably between −5° C. and −12° C. The cold applied to the skin should generate a temperature preferably between −5° C. and −12° C. for 2 to 10 seconds, to act on the melanocytes and the melanin cyto-selectively. Therefore, the application of a fluid at a temperature between −5° C. and −12° C. for a period of 2 to 10 seconds, acts on the melanin and the melanocytes, without damaging the keratinocytes, according to a principle of cyto-selectivity, that is, a cell selectivity by cryogenics. The balance between the benefits (action on the melanin and melanocytes between −5° C. and −12° C.) and the risks (destruction of the keratinocytes below −20° C.) is therefore high and, according to the invention, is consistent with high safety with the use of the cosmetic treatment and the absence of adverse effects (pain and scars).

The water condensation properties of certain cooling fluids are more pronounced than others. This is the case of dimethyl ether, a cryogenic fluid used in certain products to treat warts. When this mixture enters a foam tip, the water vapour in the air condenses due to the contact of the cold foam with the surrounding air. Systematically, the formation of droplets can be observed. They immediately freeze on the surface of the nozzle when the latter is held in the open air. This fluid remains longer in liquid form on the skin. It evaporates slowly, trapped in the tip. When this nozzle is applied to the skin, a certain amount of water is deposited on the treated area and this moisture greatly heightens the sensation of pain. However, difluoroethane (code 152A) evaporates very quickly, allowing the cold to penetrate more quickly into the skin. The speed of evaporation and spray without direct skin contact avoids the condensation of water and its "imprisonment". Difluoroethane (152A) has been selected for its boiling point at −25° C., its vapour pressure of 5.3 bars at 20° C., and its low latent heat of evaporation (160 KJ/kg), to produce a highly volatile fluid to prevent the formation of drops on the skin and, as a result, the sensation of pain while providing enough cold to be effective.

When the skin is subject to a source of cold applied on its surface, it undergoes a rapid lowering of its temperature. In this case, the application of a stream of difluoroethane without direct contact on the skin produces a variation in the surface temperature of about 10 to 20° C. per second. It thereby helps reduce the temperature of the tissue from about 34° C. to −5° C. to −12° C., a difference of about 40° C., within a little more than 2 seconds and, in practice, from 2.5 to 3 seconds, due to thermal loss.

An alternative embodiment of the invention uses gas 134A, that is, tetrafluoroethane.

The change in temperature progresses at a rate of 0.5 to 1 mm per second through the layers of the skin.

As a result, the temperature of the basal layer generated by the cold equals the temperature at the surface of the skin in a time interval of about 0.2 seconds.

In these conditions, in less than 1 second, the temperature of the melanocytes in the basal layer is identical to that of the skin surface. A spraying time of the cryogenic fluid of about 3 seconds is thereby optimal for the desired effect.

In a preferred embodiment, the method is implemented using a direction difluoroethane (152A) diffuser with automated timing system, pre-set at three seconds. The main components are described below.

Figure 3:
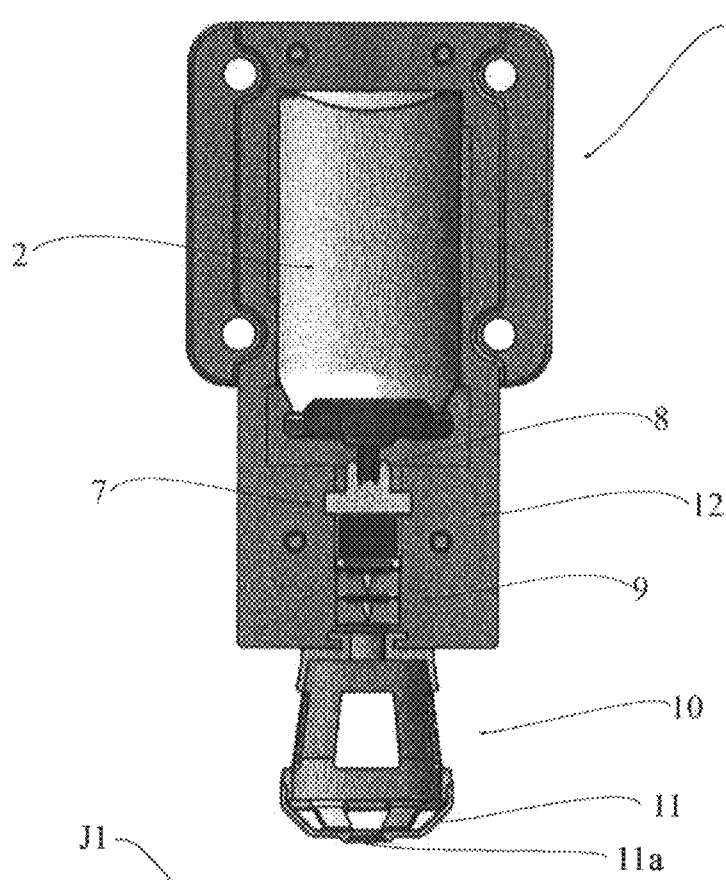
FIG. 3 is a longitudinal section view of an alternative embodiment of the cyto-selective cryogenic device according to the invention.

As shown in FIGS. 1 and 3, the components of the device are surrounded by casing 1. This casing contains a cartridge 2 of cryogenic fluid, preferably 152A, possibly 134A (tetrafluoroethane) under a pressure of about 6 bars and a maximum of 10 bars. Cartridge 2 is connected to solenoid valve 7 via a stem 8 allowing the fluid to escape from the interior of the cartridge outwards. When the device is in rest position, stem 8 lets the fluid enter the upstream chamber of solenoid valve 7. Casing 1 contains a power source, for example, in the form of electric batteries 3. The power source is connected via a switch 5 to an electronic timing system 4, which allows for the passage of fluid in solenoid valve 7 for a pre-determined time. The electronic timer 4, and consequently solenoid valve 7 is triggered by a release button 6. Downstream from solenoid valve 7, a nozzle 9 is arranged. This is presented diagrammatically according to two variants in FIGS. 1 and 3. This unit allows provides a precise and reproducible dose of cryogenic fluid being ejected via the nozzle for a pre-determined time, for example three seconds, with an accuracy of 0.1 seconds. The precision of the timing of the solenoid valve is required to secure a selective cryo-cyto action thereby avoiding reaching temperatures that are harmful for the keratinocytes.

Preferably, the end of the stem 8, which is engaged inside the cartridge 2, is equipped with a coaxial socket (not shown) containing longitudinal peripheral slots allowing for the passage of the cryogenic fluid under pressure.

These slots are designed to let the fluid pass through when the device is oriented vertically with cartridge 2 in the up position (head down).

This configuration prevents the use of the device in other positions for safety reasons. It also optimises the ease of handling of the device on the dark spots of the hand by a diffusion from top down, only using the other hand, without the help of a third person.

The nozzle 9 opens into a nozzle 10 arranged outside the casing 1. Nozzle 10, which is conical in the embodiment shown in FIG. 1, terminates with a connector 11 with an opening allowing for the contact between the stream of cold fluid (in gas state) and the targeted skin area. The aperture may thereby have an area corresponding to the diameter of the most extensive lentigines that can be treated in a cosmetic procedure without the risk of confusion with a possible melanoma. The aperture may, for example, have a circular shape with a diameter of 6 mm. Therefore, a skin spot may be treated with a single application. The conical shape of the nozzle, its length of about 35 mm, the lateral openings and the tip are designed to focus the diffusion of the fluid on a specific area of tissue.

In the embodiment presented in FIG. 1, the cryogenic fluid passes successively from cartridge 2 and stem 8, where the outlet diameter may vary from 3 to 4 mm, to the solenoid valve 7, whose input and output diameters may vary from 0.15 mm to 0.25 mm.

The cryogenic fluid passes into a chamber of the solenoid valve 7 along a length, which may range from 10 to 30 mm.

At the outlet of the solenoid valve, it enters through an opening in the nozzle 9, in which the length of the path of the fluid ranges from 3 to 12 mm, with an inner diameter of 0.15 to 3.5 mm and which may be composed of the assembly of one or several identical components of hydrophobic material and without or with a very low thermal conductivity.

This nozzle consists of an element that is long and especially narrow in which the fluid flows before it is ejected and its expansion to atmospheric pressure or to the area adjacent to the area of skin to be treated. Precisely this expansion is the endothermic phenomenon producing the cryogenic effect.

The nozzle helps reduce the initial speed of the cryogenic fluid and promotes the projection of the cold liquid sprayed on an area of skin in appropriate conditions of temperature and time set by the cosmetic care provided by the invention.

In the context of the invention, changes in the diameter, length and shape of the nozzle 9 have been found to considerably influence the flow of the gas and these modifications pay a major role, in combination with adjustments to the opening time of the solenoid valve 7, on the temperature at the surface of the affected skin area.

In particular, and according to a particularly preferred embodiment, a nozzle in which the path length of the fluid ranges from 3 to 12 mm for a inner diameter of passage of 0.15 to 3.5 mm, in combination with a time of opening of the solenoid valve of three seconds, provides a temperature range leading to an effective cryo-cyto-selective action on the treated area of tissue.

Figure 2:
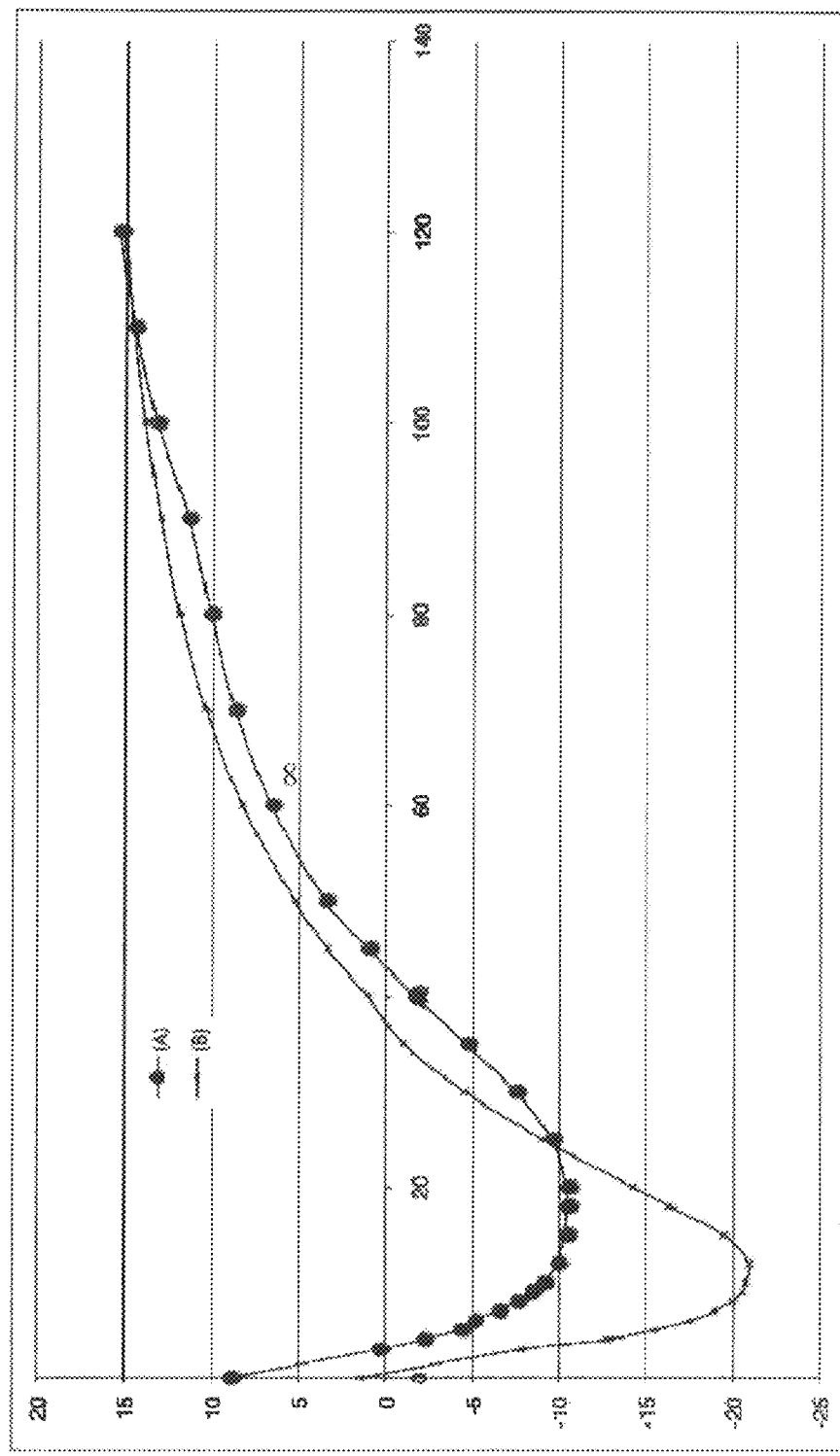
FIG. 2 is an experimental curve showing the thermal effect obtained with the device according to FIG. 1.

FIG. 2 illustrates the above by showing the temperature of the skin surface obtained after three seconds of opening of the solenoid valve with (A) and without (B) the nozzle 9 of the invention. The absence of nozzle does not provide the temperature range for a cryo-cyto-selective action since a temperature would be obtained that is harmful for the keratinocytes.

In addition, in order to avoid, on the one hand, icing phenomena and protect the means for the delivery of fluid and, in particular, insulate the electronic or mechanical components of the timing system of the solenoid valve from low temperatures and limit, on the other hand, the power of the flow, the invention defines a specific nozzle to increase the resistance to the flow of the cryogenic fluid downstream from the solenoid valve 7.

Figure 4A:
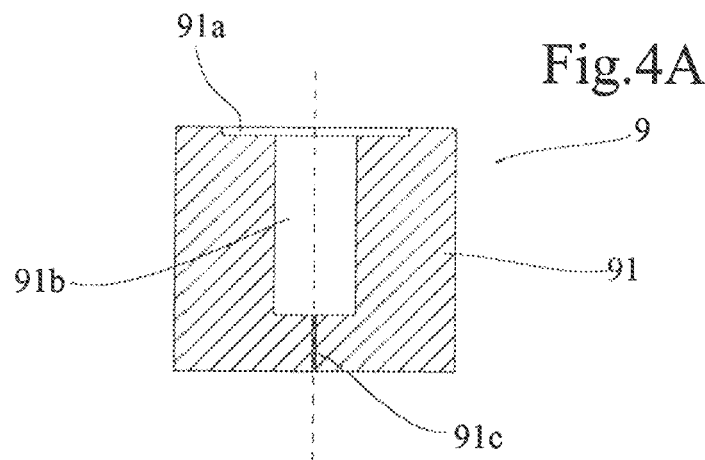
FIGS. 4A, 4B and 4C represent sectional detailed views of three variants of improved nozzles that may be used in the device of the invention.
Figure 4B:
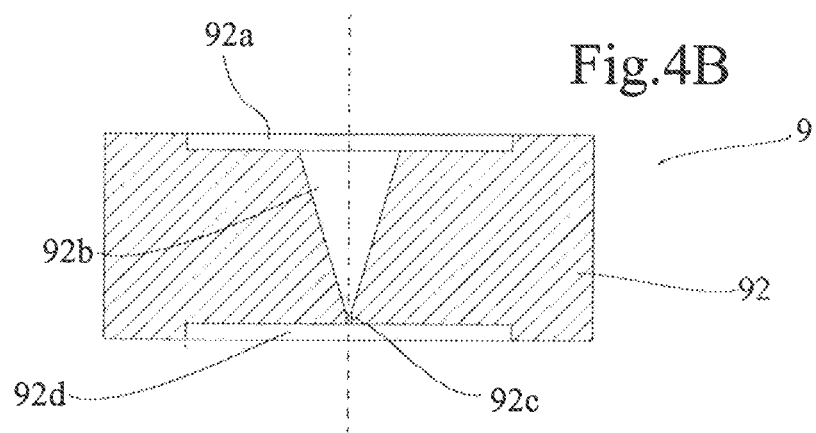
Figure 4C:
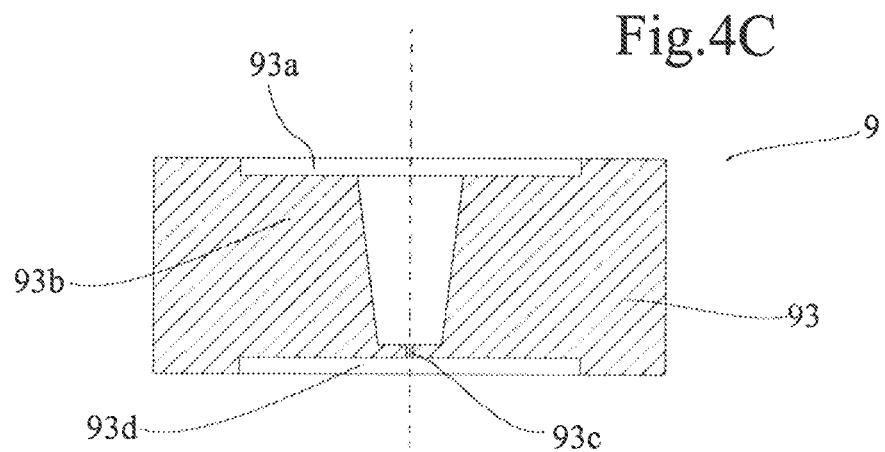

FIGS. 4A to 4C present variations of an improved nozzle according to the invention.

The nozzle 9 shown in FIG. 4A comprises a one-piece cylindrical body 91 on the upper side of which an upstream circular cavity 91a is formed.

The height of the body 91 here is between 4 and 12 mm and, preferably, 10.50 mm, and it has an outer diameter of about 12 cm while the cavity 91a has a small depth (about 0.40 mm) and an inner diameter of about 8 mm.

This cavity is made to receive an annular seal (such as J1 in FIG. 5) whose thickness roughly corresponds to the depth of the cavity 91a.

The cavity 91a extends downstream and within the body via an also cylindrical axial conduit 91b for the passage of fluid whose inner diameter is 3.5 mm here and whose length is between 8 and 9 mm.

In view of the relative dimensions, the conduit 91b forms a chamber for the transient retention and accumulation of fluid thereby ensuring, the slowing down of the flow. The fluid is then ejected downward and outward towards the skin area to be treated, successively, through an axial channel 91c of very small diameter (between 0.15 and 0.25 mm) with respect to that of conduit 91b and then the nozzle 10, whose length is preferably from 0.3 to 2.4 mm.

In conduit 91b, the stream of fluid leaving the solenoid valve 7 is at least partially liquid because the expansion is still only partial and it is subject to turbulence resulting from the impact of the stream of fluid released and sprayed from the solenoid valve 7 against the walls of the conduit. This regime of turbulence also helps slow down the flow of fluid.

Figure 5:
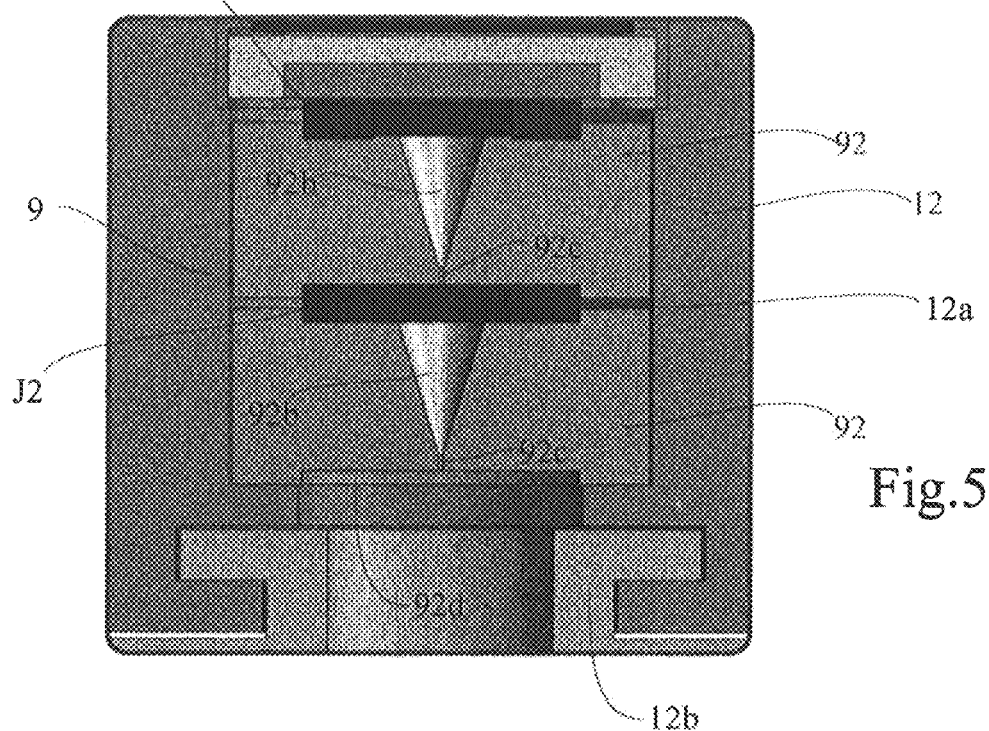
FIG. 5 shows a detailed view in longitudinal section of a variant of the nozzle used in the device in FIG. 3.

Another variant of the nozzle in the invention is illustrated by FIG. 4B in connection with FIG. 5.

The cavity 92a, like cavity 91b, is made to receive an annular seal (refer to J1, J2 in FIG. 5) whose thickness substantially corresponds to the depth of this cavity.

However, unlike the conduit 91b of FIG. 4A, the axial conduit 92b is conical with an upstream inlet diameter between 2 and 3 mm for a length between 3 and 5 mm.

The conduit 92b extends by an axial channel 92c of very small diameter (between 0.15 and 0.25 mm) and very short length (between 0.3 and 2.4 mm and, preferably, 0.5 mm) that opens to the outside down the centre of an inside coaxial cavity 92d that is identical to the upper cavity 92a and is made to also receive an identical annular seal (refer to FIG. 5).

FIG. 4c shows yet another variant of the nozzle 9 of the invention where the inner axial conduit 93b is frusto-conical with an inlet diameter upstream between 2.0 and 3.0 mm and an inside diameter in the lower part between 1.0 and 2.0 mm.

The conduit 93b opens into the lower cavity 93d via a channel 93c identical to channel 92c of FIG. 4B.

To ensure a better thermal insulation of the solenoid valve 7 and, in particular, the electronic or mechanical system providing the time delay, with respect to the low temperatures of the fluid immediately entering downstream in the nozzle 9, according to the invention, it is envisaged to make the body of the nozzle out of a hydrophobic material and without or with very low thermal conductivity such as PTFE, PFA, POM or a POM+PTFE mixture. Indeed, these materials do not retain drops of water (neither by absorption, nor adsorption) and thereby eliminate the risk of icing of the nozzle.

Moreover, since these materials are thermally insulating, they protect the timing system, whether electronic or mechanical, avoiding malfunction.

Advantageously, the nozzle body may be created by moulding the hydrophobic and thermally non-conductive plastic.

FIG. 5 presents a variant of the nozzle of the invention made by the assembly and connection in series of two identical bodies 92 as shown in FIG. 4B.

However, it would be possible, without departing from the scope of the invention, to provide the assembly and fluid connection of two bodies of different dimensions and profile, in particular, according to variants illustrated by FIGS. 4A to 4C.

Each of the two bodies 92, as illustrated in FIG. 4B, is cylindrical and has a circular upstream cavity 92a like the cavity 91a in FIG. 4A in which at least one annular seal J1, J2 is housed.

The diameter of the two bodies 92 is about 12 mm like the body 91 in FIG. 4A and their respective height is between 4.5 and 5.5 mm.

The two bodies 92 are assembled against each other in a stacked and coaxial manner overwhelming the joints J, respectively, upper J1 and intermediate J2, inside the upstream compartment 12a of a casing 12 whose dimensions are designed for this purpose.

The in series connection of the conduits 92b, 92c of at least two bodies 92 of nozzle 9 downstream from the solenoid valve 7 limits and/or slows down the flow of cryogenic fluid, thereby at the same time avoiding an overly sudden expansion which is likely to cause icing and a low temperature on the skin application area.

According to a preferred embodiment, the diameter of conduit 92c is 0.17 mm over a height between 0.5 and 0.9 mm and preferably 0.5 mm.

Preferably, the casing 12 will be made in one piece with the housing 1 (FIGS. 1 and 3) and is connected via a downstream compartment 12b made in the lower part, to the nozzle 10 communicating with the end-piece 11 forming a collimator.

FIGS. 3 and 5 illustrate a method of connection of the nozzle 10 and tip 11 to the casing 12 of the nozzle 9.

According to one variant, it would be possible to provide a releasable connection (for example, by bayonet) and/or adjustable in height (for example, by screwing) of the nozzle 10 on the casing 12 so as to adjust the position of the tip and the cryogenic fluid concentration over the target area to be treated.

In the variant shown in FIG. 3, the end-piece 11 is designed as a perforated shell with a central opening 11a for the focused application of the fluid on the skin area.

The lateral wall of this shell is perforated and its periphery is snapped over the peripheral edge of the lower part of the nozzle 10.

The invention will be described in further detail in the following example for the implementation of the method of treatment.

Example of the Implementation of the Method of Cosmetic Treatment in the Invention by Cyto-Selective Cryogenics.

A study was carried out to validate the device described above. The study consisted of applying a cryogenic gas 152A on subjects with dark spots on the back of the hand. The study included 4 subjects, two men and two women, JMPAT, CDEN, AMAH and YPHIL, 50, 57, 59 and 55 years old respectively. The duration of the application of the cryogenic gas was set at 3 seconds.

The subjects had the following characteristics:

JMPAT: presence of a very visible dark spot on the right hand, near the index.

CDEN: presence of a visible dark spot on the right hand, between the index and the little finger.

AMAH: presence of two large dark spots, on the right hand.

YPHIL: presence of two dark spots, almost touching, on the right hand.

The results show that the device eliminates dark spots after one spray of 3 seconds per spot. Indeed, the treated dark spots totally disappeared in all of the patients after a period of two to three weeks after a single application. Some of the subjects enrolled in the study were already treated by a dermatologist on other similar dark spots on the back of their hand. The treatment consisted of the application of traditional cryotherapy with nitrogen or dimethyl ether.

Unlike these treatments, the surface application of cryogenic cold with the device in the invention did not induce a sensation of pain, even though the subjects felt sharp pain during the previous treatment by the dermatologist. In addition, the absence of major inflammation and tissue destruction likely to lead to marks in the form of scars or hypo-pigmentation is noted.

These observations confirm that the device really provides a cryo-cyto-selective cosmetic effect, while traditional cryotherapy with nitrogen or dimethyl ether, as carried out under medical supervision in the office of a dermatologist, did not provide such an effect. The device with its cryo-cyto-selective action does not provoke destruction by necrosis of all of the tissue, or the destruction of keratinocytes and therefore does not provoke the phenomena observed with traditional cryotherapy with nitrogen as performed in the office of a dermatologist (inflammation, severe pain, scarring, hypo-pigmentation).

Although presented in FIG. 1 in the form of an elongate diffuser designed to contain a cartridge of difluoroethane, the invention may apply to any cryogenic fluid diffuser having a boiling temperature between −20° C. and −65° C. and a latent heat evaporation between 1 and 500 KJ/Kg, equipped with a suitable focusing device on an area of skin and a pre-set or adjustable system of timing control.

As described above, the invention provides a method for the cosmetic treatment of skin tissue to obtain a cryo-cyto-selective action on melanocytes versus keratinocytes. As already noted above, the term cryo-cyto-selective action or cryo-cyto-selectivity refers to a selective action on a population of cells of a certain tissue without acting on at least one other or other populations of cells.

The invention may be applied to other types of populations of cells in other tissues. The term population of cells is understood in its broadest sense, that is, a set of cells having the same characteristics, for example, a type of cell, a cell line, stem cells, prokaryotes or eukaryotes, of all origins, human, animal or plant.

In addition, the method in the invention may also apply to the components of cells, that is, cell organelles, including but not limited to melanosomes, nucleoli, nuclei, ribosomes, vesicles, endoplasmic reticuli, Golgi, cytoskeletons, mitochondria, vacuoles, cytosols, lysosomes, centrosomes and plasma membranes.

The method in the invention as described above may also apply, provided that it is possible to determine a deleterious temperature range for the cell population, structures or target organisms, and in which range another population or surrounding tissue is not affected in a noteworthy or unacceptable manner.

The invention claimed is:

1. Device for implementing a method of treatment of dark spots on the skin, comprising:
    a reservoir of cryogenic fluid,
    a solenoid valve for the passage of the cryogenic fluid downstream, from the inside of said reservoir towards an ejection nozzle and via a flow limiting nozzle,
    wherein said solenoid valve is associated with an electronic timing system allowing the solenoid valve to be opened for a specific pre-determined time with an accuracy of 0.1 second, and
    wherein said flow limiting nozzle comprises at least one body equipped with at least one inner conduit that is axial and cylindro-conical.

2. The device of claim 1, wherein said nozzle is made of a hydrophobic, non heat-conductive material.

3. The device of claim 1, wherein said at least one inner conduit has a length between 3 and 12 mm and an inner diameter between 0.15 and 3.5 mm.

4. The device of claim 1, wherein said flow limiting nozzle comprises two bodies assembled by stacking and then crushing at least one intermediate seal so that the inner conduits of the two bodies are connected coaxially in series.

5. The device of claim 1, wherein said at least one body is equipped with cavities, respectively, upper and bottom for receiving intermediate sealing joints.

6. The device of claim 1, wherein said at least one body comprises two internal conduits, respectively, an upstream conduit at least partially conical forming a retention chamber and opening downstream in a cylindrical conduit of smaller diameter.

7. Device according to claim 1 wherein said flow limiting nozzle delivers a stream of cryogenic fluid with a pressure up to 10 bars.

* * * * *